United States Patent
Lunn et al.

(10) Patent No.: US 10,582,920 B2
(45) Date of Patent: Mar. 10, 2020

(54) DISTAL TIP TWO PIECE EXTERNAL EXPANSION ANCHOR

(71) Applicant: Smith & Nephew, Inc., Memphis, TN (US)

(72) Inventors: Richard M. Lunn, Kingston, MA (US); Timothy Young, Natick, MA (US); Matthew Edwin Koski, Westford, MA (US); John Slusarz, Hopedale, MA (US); Paul R. Duhamel, Groton, MA (US); Wei Li Fan, Boston, MA (US); Steven Astorino, Norfolk, MA (US)

(73) Assignee: Smith & Nephew, Inc., Memphis, TN (US)

( * ) Notice: Subject to any disclaimer, the term of this patent is extended or adjusted under 35 U.S.C. 154(b) by 150 days.

(21) Appl. No.: 14/903,686

(22) PCT Filed: Mar. 6, 2014

(86) PCT No.: PCT/US2014/021302
§ 371 (c)(1),
(2) Date: Jan. 8, 2016

(87) PCT Pub. No.: WO2015/005951
PCT Pub. Date: Jan. 15, 2015

(65) Prior Publication Data
US 2016/0157849 A1    Jun. 9, 2016

Related U.S. Application Data

(60) Provisional application No. 61/844,674, filed on Jul. 10, 2013.

(51) Int. Cl.
*A61B 17/04* (2006.01)

(52) U.S. Cl.
CPC .. *A61B 17/0401* (2013.01); *A61B 2017/0412* (2013.01); *A61B 2017/0414* (2013.01);
(Continued)

(58) Field of Classification Search
CPC ........ A61B 17/0401; A61B 2017/0424; A61B 2017/0414; A61B 2017/0412; A61B 2017/0445
See application file for complete search history.

(56) References Cited

U.S. PATENT DOCUMENTS

| 5,354,298 A | 10/1994 | Lee et al. |
| 5,464,427 A | 11/1995 | Curtis et al. |

(Continued)

FOREIGN PATENT DOCUMENTS

WO    1998038938 A1    9/1998

OTHER PUBLICATIONS

International Preliminary Report on Patentability from related International Application No. PCT/US2014/021302 dated Jan. 12, 2016.
(Continued)

*Primary Examiner* — Julian W Woo
(74) *Attorney, Agent, or Firm* — Burns & Levinson LLP; Joseph M. Maraia

(57) ABSTRACT

Examples of a suture anchor (100) having a non-expandable body (105) and expendable cap (110) are described herein. In response to an axial insertion force that brings the non-expandable body and expendable cap together inside a bone hole, the expendable cap expands radially. This creates a radial force of expansion that advantageously augments an interference fit between the suture anchor and bone hole, which leads to higher fixation strength. Other examples include retention features that inhibit the expendable cap from returning back into its unexpanded state. This advantageously maintains the radial force of expansion against the (Continued)

surrounding pressure of the walls of the bone hole pressing back on the suture.

18 Claims, 9 Drawing Sheets

(52) U.S. Cl.
CPC ............... *A61B 2017/0424* (2013.01); *A61B 2017/0445* (2013.01)

(56) References Cited

U.S. PATENT DOCUMENTS

| | | | |
|---|---|---|---|
| 5,486,197 A | 1/1996 | Le et al. | |
| 5,545,180 A | 8/1996 | Le et al. | |
| 5,643,321 A | 7/1997 | McDevitt | |
| 5,645,589 A | 7/1997 | Li | |
| 5,935,129 A | 8/1999 | McDevitt et al. | |
| 6,524,316 B1 * | 2/2003 | Nicholson | A61B 17/0401 411/45 |
| 6,692,516 B2 * | 2/2004 | West, Jr. | A61B 17/0401 606/232 |
| 7,381,213 B2 * | 6/2008 | Lizardi | A61B 17/0401 606/232 |
| 7,867,264 B2 * | 1/2011 | McDevitt | A61B 17/0401 606/313 |
| 8,162,978 B2 * | 4/2012 | Lombardo | A61B 17/0401 606/232 |
| 8,348,982 B2 * | 1/2013 | Baynham | A61B 17/686 606/294 |
| 8,419,780 B2 * | 4/2013 | Bickley | A61B 17/686 606/286 |
| 9,414,834 B2 * | 8/2016 | Palese | A61B 17/0401 |
| 9,463,009 B2 * | 10/2016 | Sack | A61B 17/844 |
| 10,201,344 B2 * | 2/2019 | Palese | A61B 17/0401 |
| 2001/0049529 A1 | 12/2001 | Cachia et al. | |
| 2002/0072797 A1 * | 6/2002 | Hays | A61F 2/0811 623/13.14 |
| 2005/0075668 A1 | 4/2005 | Lizardi | |
| 2009/0149883 A1 | 6/2009 | Brunsvold | |
| 2009/0318964 A1 * | 12/2009 | Lombardo | A61B 17/0401 606/232 |
| 2013/0158597 A1 | 6/2013 | Hernandez | |

OTHER PUBLICATIONS

EPO Communication from European Application No. 14713335.9 dated May 15, 2017.
Japanese Decision of Rejection Office Action Application No. 2016-525339 dated 8/1/18.

* cited by examiner

DISTAL TIP TWO PIECE EXTERNAL EXPANSION ANCHOR

CROSS-REFERENCE TO RELATED APPLICATIONS

This application is a National Phase application of International Application No. PCT/US14/21302, filed Mar. 6, 2014 which claims the benefit of U.S. Provisional Application Ser. No. 61/844,674, filed on Jul. 10, 2013, the disclosure of which is incorporated herein by reference in its entirety.

BACKGROUND

Surgeons use a variety of suture anchors to conduct soft tissue repair procedures. For these procedures, one or more sutures called "repair" sutures are attached to a suture anchor, which is or will be fixed to bone. The repair sutures are used to tie soft tissue down to the bone. There are many challenges to joining a repair suture to a suture anchor.

One kind of suture anchor used in soft tissue repair procedures is secured into/within bone through an interference fit with a pre-drilled bone hole. Maximum interference fit is desirable because it results in higher bone fixation strength and less chance of the anchor pulling out of bone. The issue arises, however, when attempting to obtain the maximum interference fit with small diameter anchors (e.g., on the order of 1 mm-3 mm).

As anchors decrease in diameter without height change, their column strength also decreases. Lower column strength makes it more difficult to insert small diameter anchors into bone, especially when the bone is dense. In short, because small diameter anchors are less structurally sound and require greater force to insert them, there is an increased risk of small diameter anchors failing when inserting them.

Another kind of suture anchor used in soft tissue repair is an expanding suture anchor. Expanding the suture anchor inside a bone hole creates a radial force of expansion. This force presses against of the walls of the bone hole and secures the anchor to the bone. One of the problems with the expanding anchor is that once expanded, there is no way of knowing that the expansion of the anchor has been retained with surrounding pressure from the bone hole pressing back in on the radial force of expansion.

SUMMARY

Described herein are examples of a suture anchor for soft tissue repair that address the foregoing shortcomings and others as well. In one aspect, at least one example described herein provides a suture anchor. The suture anchor includes a cannulated non-expandable body comprising a distal end having a first portion and a second portion, a proximal end configured to engage a suture anchor insertion instrument, and a plurality of projections extending, radially, from an outer surface extending between the distal end and proximal end. The plurality of projections configured to compress into bone. The suture anchor also includes an expandable cap defining a cavity configured to engage the distal end of the cannulated non-expandable body. The cavity has a diameter larger than the first portion and smaller than the second portion that allows the expandable cap to expand radially outward and compress into the bone during engagement of the distal end of the cannulated non-expandable body and the expandable cap. The suture anchor also includes a suture extending from the cavity of the expandable cap and slidably received within the cannulatation of the non-expandable body.

In another example, the suture anchor may further include one or more of the following, alone or in any combination. In some examples of the suture anchor, the distal end is a truncated conical section having a first diameter and a second diameter larger than the first diameter. In some examples of the suture anchor, the first portion of the distal end does not engage a surface of the cavity and the second portion of the distal end engages the surface of the cavity.

The proximal end may include a protrusion or recess configured to engage a complementary recess or protrusion, respectively, of a suture anchor insertion instrument. The plurality of projections may comprise a plurality of annular ribs, wings, or a combination of annular ribs and wings.

The cavity may have a shape complementary to the distal end of the cannulated non-expandable body. In some examples of the suture anchor, the suture comprises an eyelet extending from the expandable cap.

The expandable cap may further comprise a terminal surface adjacent the cavity defining a first aperture, a second aperture, and a bridge separating the first aperture and the second aperture. In this examples, the suture extends around the bridge, and a first free end and a second free of the suture are routed through the first aperture and second aperture, respectively, and through the through hole toward the proximal end of the cannulated non-expandable body. The first free end and the second free may be coupled together.

The expandable cap comprises a distal end and a proximal end, and may further comprise at least one expansion slot formed in the proximal end of the expandable cap. In one example, the at least one expansion slot is aligned with the axis of the cannulated non-expandable body.

The distal end of the cannulated non-expandable body may further comprise a locking insert tab and the expandable cap may further comprise a holding insert tab configured to engage the locking insert tab. When the locking insert tab and holding insert tab are engaged, the expandable cap and the cannulated non-expandable body are locked together. In some examples, the distal end of the cannulated non-expandable body may comprise an annular protrusion and the expandable cap may comprise an annular groove configured to engage the annular protrusion. When the annular groove and annular protrusion are engaged, the expandable cap and the cannulated non-expandable body are locked together.

Other examples of the suture anchor further include a post extending, axially, from the cavity of the expandable cap. The cannulation of the non-expandable body is configured to receive the post and align the non-expandable body and the expandable cap.

Some examples of the suture anchor include at least one protrusion formed on the outer surface of the cannulated non-expandable body at the distal end. In these examples, the at least one expansion slot is configured to receive the at least one protrusion and align the cannulated non-expandable body and the expandable cap.

The cannulated non-expandable body may be made from a first material and the expandable cap may be made from a second material more flexible than the first material. The cannulated non-expandable body may have a diameter between 1 mm and 3 mm. The cannulated non-expandable body may comprises a material selected from a formulation of poly(lactic-co-glycolic) acid (PLGA), ß-Tricalcium phosphate (ß-TCP) and calcium sulfate, poly-L-lactic acid-hydroxyapatite (PLLA-HA), polyether ether ketone (PEEK) or variants thereof.

In another aspect, at least one example described herein provides a procedure for soft tissue repair. The procedure includes providing any example of the suture anchor described herein. The procedure also includes inserting the suture anchor into a hole prepared in bone. The procedure also includes expanding the expandable cap by applying a force aligned with a longitudinal axis extending between distal end and proximal end of a cannulated non-expandable body of the suture anchor. The procedure also includes tying soft tissue down to the bone using a repair suture coupled to the suture. Expanding the expandable cap may include pulling the expandable cap over the distal end of the cannulated non-expandable body using the suture. Alternatively, expanding the expandable cap may include pushing the distal end of the cannulated non-expandable body into the cavity of the expandable cap using a suture anchor insertion instrument. In yet another example, expanding the expandable cap may include a combination of pulling the expandable cap over the distal end of the cannulated non-expandable body using the suture and pushing the distal end of the cannulated non-expandable body into the cavity of the expandable cap using the suture anchor insertion instrument. The procedure also includes drilling the hole into the bone.

BRIEF DESCRIPTION OF THE DRAWINGS

The accompanying drawings, which are incorporated in and form a part of the specification, illustrate examples of the present disclosure and together with the written description serve to explain the principles, characteristics, and features of the disclosure. In the drawings.

DESCRIPTION

In the following detailed description of the illustrated examples, reference is made to accompanying drawings, which form a part thereof, and within which are shown by way of illustration, specific examples, by which the subject matter can be practiced. It is to be understood that other examples can be utilized and structural changes can be made without departing from the scope of the disclosure.

The particulars shown herein are by way of example and for purposes of illustrative discussion of the examples only and are presented in the case of providing what is believed to be the most useful and readily understood description of the principles and conceptual aspects of the disclosure. In this regard, no attempt is made to show structural details of the subject matter in more detail than is necessary for the fundamental understanding of the disclosure, the description taken with the drawings making apparent to those skilled in that how the several forms of the present disclosure can be embodied in practice. Further, like reference numbers and designations in the various drawings indicate like elements.

Figure 1:
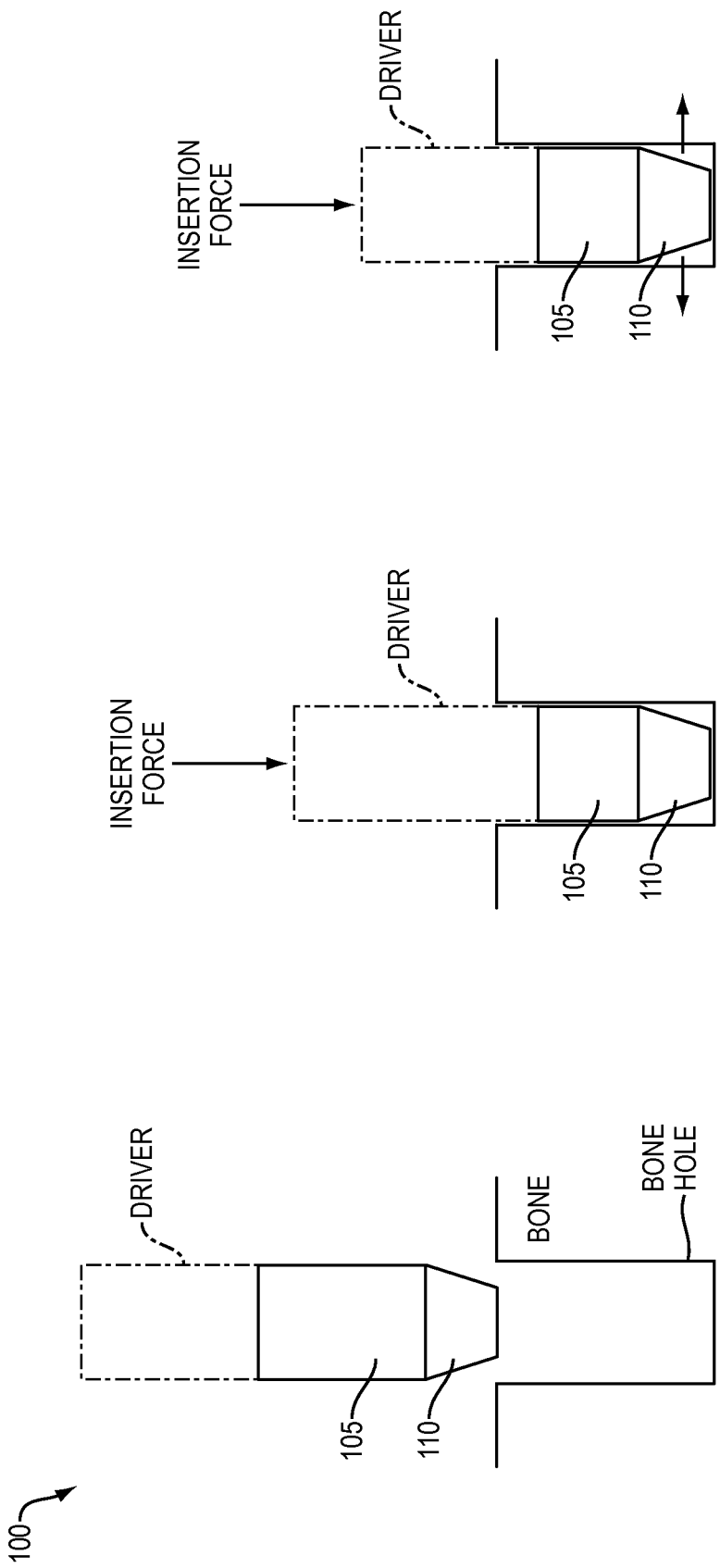
FIGS. 1A-1C are side views on a suture anchor with a non-expandable body and an expandable cap being inserted into bone.

FIGS. 1A-1C, show an example suture anchor 100 including a non-expandable body 105 and expandable cap 110. The suture anchor 100, in an undeployed state, is at an end of a suture anchor insertion instrument (shown in phantom outline). A surgeon uses the instrument to insert the suture anchor 100, distal end first, into the bone hole. The surgeon then pushes on or hits (shown as an insertion force) the instrument to push the suture anchor 100 into the bone hole. The suture anchor 100 moves into the hole until the desired insertion depth is reached. The desired insertion depth may be controlled, for example, by a positive stop feature between a drill guide and the driver, or when a mark on the driver matches up with a respective line on a drill guide. The surgeon continues to push on the instrument to push the non-expandable body 105 into the expandable cap 110. That is, the proximal portion of the suture anchor 100 is protracted against the distal portion. This action expands the expandable cap 110 outward, radially, into the bone hole and secures the suture anchor 100, now in the deployed state, in the bone hole. In the deployed state, the distal portion of the suture anchor 100 has a larger outer diameter than the proximal portion of the suture anchor 100.

In another mode of operation, the surgeon pulls on a suture attached to the expandable cap 110, which is routed through a cannulation (or through hole) running the length of the non-expandable body 105, to pull the expandable cap 110 onto the body 105. That is, the distal portion of the suture anchor 100 is retracted against the proximal portion. In turn, the expandable cap 110 expands outward, radially, into the bone hole and secures the suture anchor 100 in the bone hole. In yet another mode of operation, the surgeon does a combination of pushing the non-expandable body 105 into the expandable cap 110 and pulling the expandable cap 110 onto the non-expandable body 105 to expand the expandable cap 110 into the bone hole and secure the suture anchor 100 in the bone hole.

Figure 2:
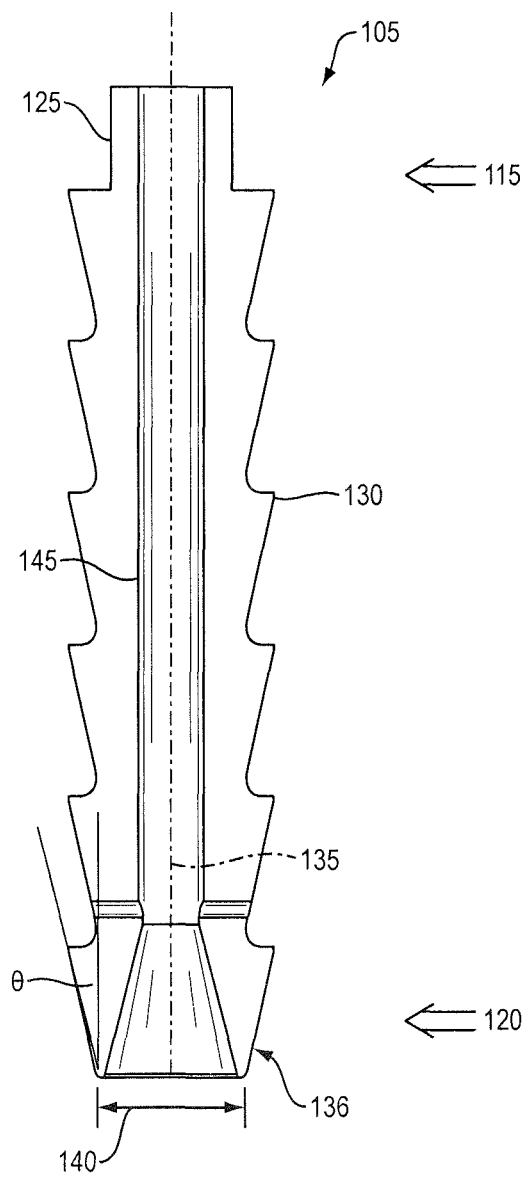
FIG. 2 is a sectional view of an example of the non-expandable body.

FIG. 2 shows an example of the cannulated non-expandable body 105 (or simply referred to as non-expandable body) having a proximal end 115, distal end 120, and longitudinal axis 135 extending between the proximal and distal ends 115, 120. A convenient example of the non-expandable body 105 has a diameter between 1 mm and 3 mm. At the proximal end 115, the non-expandable body 105 includes a protrusion 125 that mates with a complementary recess in a suture anchor insertion instrument and couples the suture anchor 100 to the instrument. Other means for coupling include, for example, a spline and a corresponding socket.

Between the proximal and distal ends 115, 120, the non-expandable body 105 includes a plurality of annular ribs. The annular ribs 130 contribute to the overall fixation strength of the suture anchor 100. The expandable cap 110 enhances or augments the fixation strength provided by the annular ribs 130. The annular ribs 130 are formed circumferentially around the non-expandable body 105. The geometry of the ribs 130 is selected based on the ability to be inserted into a bone hole and the ability to be retained in a bone hole. Other means for retaining the suture anchor 100 into a bone hole include, for example, ribs that are discontinuous and a plurality of wings.

At the distal end 120, the non-expandable body 105 includes a ramp 136 that engages and expands the expandable cap 110. (Described in more detail below.) The ramp 136 is formed at angle to the longitudinal axis 135 of the non-expandable body 105. As shown, the angle is between 20° and 45° angle. Other angles between 0° and 90° selected based on a variety of factors including manufacturability are also contemplated. For example, as shown, the geometry of the ramp 136 is substantially similar to that of the annular ribs 130. The ramp 136 has a diameter called an "engagement diameter" 140. The engagement diameter 140 is the dimension of the ramp 136 at which the non-expandable body 105 engages the expandable cap 110 and causes the expandable cap 110 to expand outward, radially, into a bone hole. The size of the engagement diameter 140 may be selected based on a specific degree of expansion (e.g., 30%-40% increase over the original size of the expandable cap 110).

Along the longitudinal axis 135, the non-expandable body 105 includes a cannulation 145 running the length of the non-expandable body 105 between the proximal and distal ends 115, 120 of the non-expandable body 105. The cannulation 145 is sized to receive a suture or a suture doubled over on itself so as to form an eyelet 190 at one end. In some examples of the non-expandable body 105, the cannulation 145 slidably receives suture(s). That is, the sutures can slide through the cannulation 145. As described in greater detail below, the cannulation 145 receives at least a portion of the suture and shelters that portion from damage from the environment.

Figure 3:
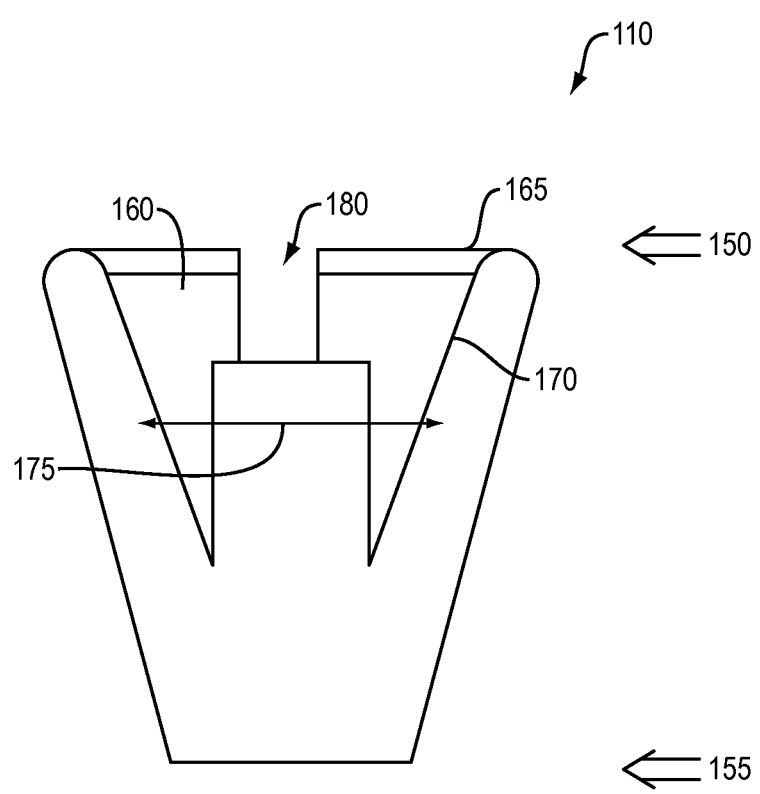
FIG. 3 is a sectional view of an example of the expandable cap.

FIG. 3 shows an example of the expandable cap 110 configured to receive the distal end 120 of the non-expandable body 105. The expandable cap 110 includes a proximal end 150, distal end 155, and cavity 160 formed by the expandable cap 110. The cavity 160 has an opening 165 at the proximal end 150 of the expandable cap 110. In some examples, the diameter of the opening 165 is larger than the engagement diameter 140 of the non-expandable body 105 and tolerates an amount of misalignment between the non-expandable body 105 and expandable cap 110.

The cavity 160 further has a surface 170 and at least one diameter, called a "receiving diameter" 175 that is the same as or smaller than the engagement diameter 140 of the non-expandable body 105. At the receiving diameter 175 of the cavity 160, the non-expandable body 105 and expandable cap 110 are engaged. The ramp 140 and surface 170 are in contact with one another. This engagement expands the expandable cap 110 outward, radially.

As shown, the surface 170 of the cavity 160 is an inverse geometry of the ramp 140 of the non-expandable body 105. The diameters of the cavity 160 are increasingly smaller than the engagement diameter 140 toward the distal end 155 of the expandable cap 110. Further engagement of the non-expandable body 105 and expandable cap 110 (either by pushing the non-expandable body 105 into the expandable cap 110, pulling the expandable cap 110 onto the non-expandable body 105, or a combination of both) pushes the ramp 140 against the surface 170 and expands the expandable cap 110 in an outward radial direction.

As shown, the expandable cap 110 has the shape of a truncated cone. Other geometries are possible. For example, the expandable cap 110 may be pointed enabling a surgeon to lift or otherwise manipulate soft tissue intraoperatively.

The expandable cap 110 further includes an expansion slot 180 contributing to the expandability of the expandable cap 110. The expansion slot 180 is formed in the expandable cap 110 and aligned with the longitudinal axis 125 of the non-expandable body 105. In some examples, the expansion slot 180 is at an angle to the longitudinal axis 125 of the non-expandable body 105. The expansion slot 180 extends from the proximal end 150 of the expandable cap 110 towards the distal end 155 of the expandable cap 110.

Another example of the expandable cap 110 has an inner surface, outer surface and wall formed from the inner surface and outer surface. The expandable cap 110 further includes an expansion slot 180 formed in the wall and aligned with the longitudinal axis 125 of the non-expandable body 105. The expansion slot 180 extends from the proximal end 150 of the expandable cap 110 towards the distal end 155 of the expandable cap 110.

Each expansion slot 180 defines a flexible wall section. The expandable cap 110 has an expanded state defined by the distal movement of the non-expandable body 105 into the expandable cap 110 and radial outward movement of the flexible wall section. The expandable cap 110 in the expanded state compresses into bone.

Figure 4A:
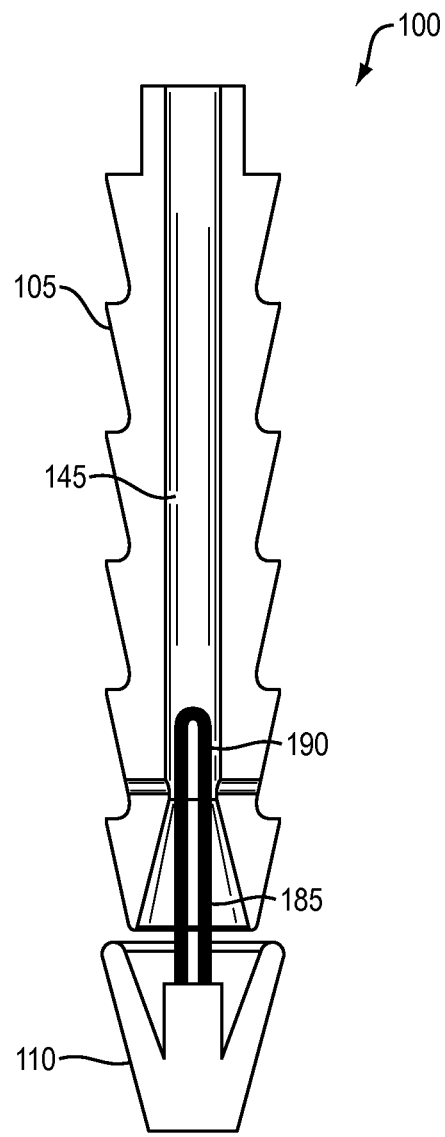
FIG. 4A is a sectional view of an example of the suture anchor.
Figure 4B:
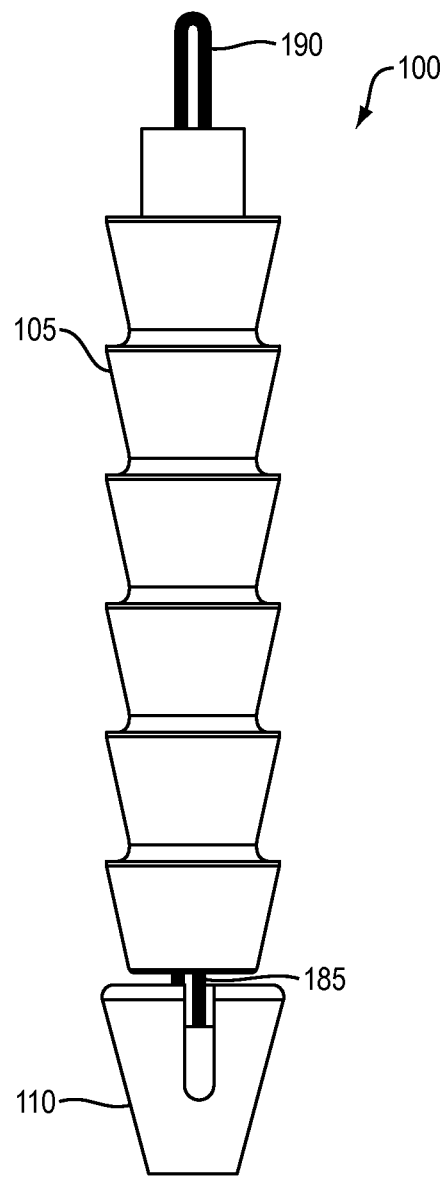
FIG. 4B is a side view of an example of the suture anchor.

FIGS. 4A and 4B show a suture 185 projecting from the cavity 160 of the expandable cap 110 and forming an eyelet 190 at one end. The eyelet 190 receives the repair suture and allows the repair suture to slide, freely. The ability for the repair suture to slide, referred to as "suture slide," is beneficial because it allows the surgeon to tie knots in the repair suture and secure the soft tissue to bone. Suture slide further allows the surgeon to position and reposition the soft tissue readily. In a typical application, the suture anchor 100 with suture 185 and repair suture are preloaded onto a suture anchor insertion instrument (e.g., as part of a surgical system) ready for a surgeon to use. The surgeon drills a hole in bone, inserts the suture anchor 100 into the hole, deploys the suture anchor 100, and then uses the repair suture to tie the soft tissue down to the correct anatomical position.

The suture 185 may be coupled to the expandable cap 110 (e.g., with an adhesive) or formed integral with the expandable cap 110 (e.g., over molded). Another example of the expandable cap 110 includes a through-hole through which the suture 185 forming the eyelet 190 is passed. A knot or mechanical knot tied at the other end the suture 185, opposite the eyelet 190, inhibits the suture 185 from being pulled through the expandable cap 110 when tensioned. Yet another example of the expandable cap 110 includes a bridge around which the suture 185 forming the eyelet 190 is passed. A knot or mechanical knot is tied at the proximal end of the anchor.

The cannulation 145 of the non-expandable body 105 is configured to slidably receive the suture 185 and eyelet 190 (suture/eyelet). As shown in FIG. 4A, the cannulation 145 receives the entire portion of the suture/eyelet. This arrangement is particularly beneficial because it protects the suture/eyelet from the surgical site environment. For example, the interface or junction between the suture/eyelet and repair suture is located inside the non-expandable body 105 and, thus, shielded from sharp edges of a bone hole.

FIG. 4B shows another arrangement in which a portion of the suture/eyelet is received by the cannulation 145 leaving a remaining portion exposed. The exposed portion of the suture/eyelet provides unobstructed access to the eyelet 190 during an operation. As such, this arrangement advantageously enables a surgeon to intraoperatively slide a repair suture (s) through the eyelet 190.

Another example arrangement has the suture/eyelet received within the cannulation 145, completely, when the suture anchor 100 is in its undeployed state. When the suture anchor 100 is in its deployed state (e.g., the non-expandable body 105 is pushed into the expandable cap 110 or vice versa, and the expandable cap 110 is expanded) a portion of the suture/eyelet is exposed.

The foregoing examples of the non-expandable body 105 and expandable cap 110 are made of the same material (e.g., polyether ether ketone or PEEK). Other examples of the non-expandable body 105 and expandable cap 110 are made from different materials. In these examples, the non-expandable body 105 is formed of a material less flexible (more stiff) then the one forming the expandable cap 110. One such example includes the non-expandable body 105 made from a bioabsorbable material and the expendable cap made from more flexible PEEK.

Examples of the suture anchor 100 can provide one or more of the following advantages. One advantage is improving the chance of insertion success because interference fit upon insertion is lower. Another advantage is increasing fixation strength through increased interference fit at the distal tip (after distal expansion). High fixation strength is obtained after the suture anchor is fully seated into a bone hole.

FIGS. 5A-5D show a suture anchor 200 with retention features. The suture anchor 200 is similar to the suture anchor 100 of FIGS. 2, 3, 4A, and 4B having a non-expendable body 205 and an expendable cap 210. The suture anchor 200, however, differs from the suture anchor 100 with the addition of retention futures, described in more detail below. In operation, owing to the geometry of the non-expandable body 205 and expendable cap 210 (described in greater detail below) the expendable cap 210 expands radially in response to an axial insertion force that brings the non-expandable body 205 and expendable cap 210 together. Complementary retention features 230 on the non-expandable body 205 and expandable cap 210 mechanically engage one another, locking the non-expendable body 205 and expendable cap 210 together. In the locked state shown in FIG. 5B, the retention features 230 inhibit the expendable cap 210 from returning or "relaxing" back into its unexpended state. Advantageously, this maintains the interference fit that provides fixation of the suture anchor 200 in a bone hole.

Figure 5A:
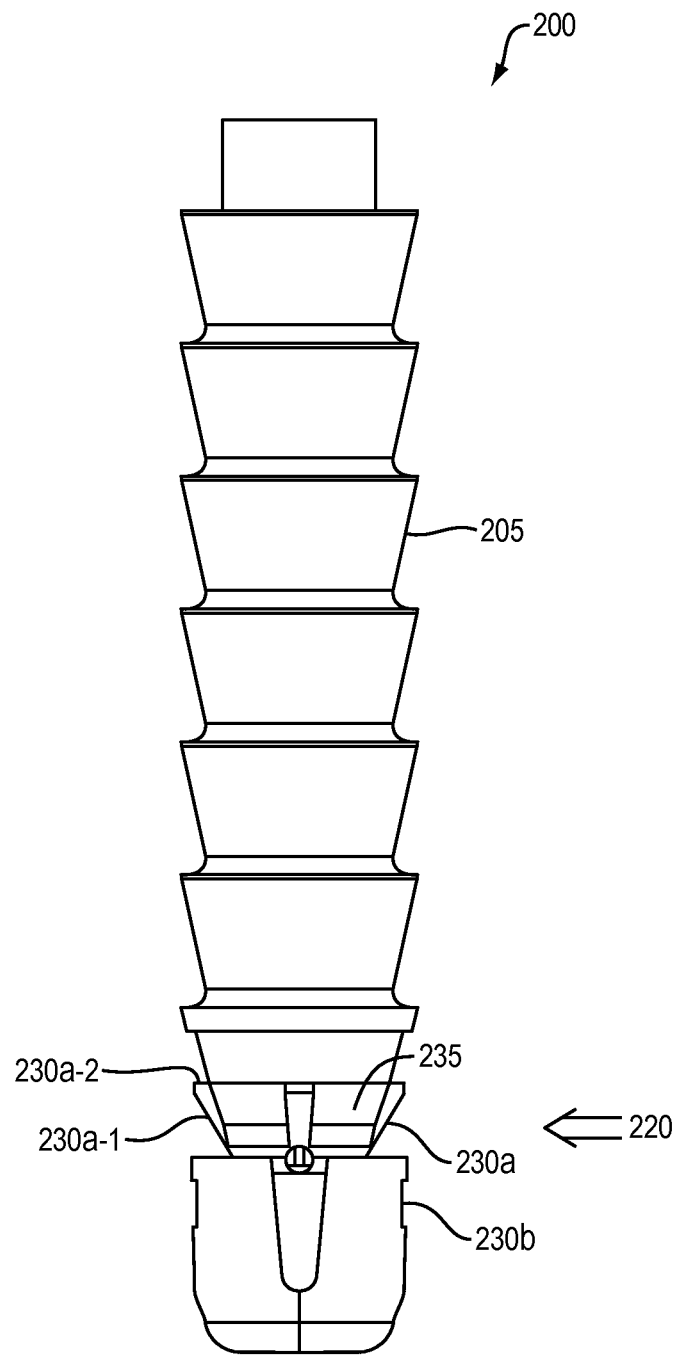
FIGS. 5A-D are views of an expandable suture anchor with a snap over cap.
Figure 5B:
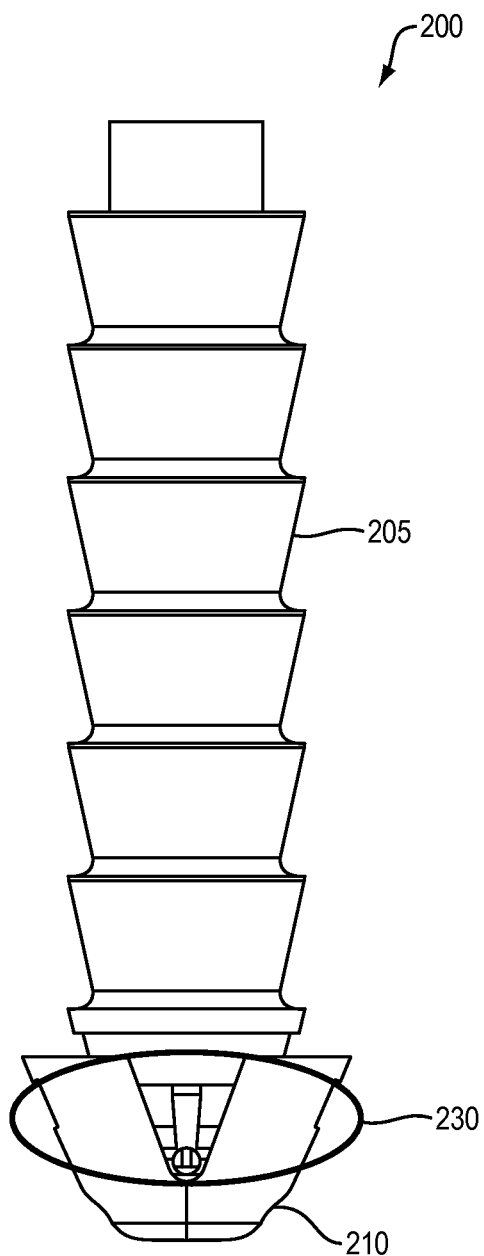
Figure 5C:
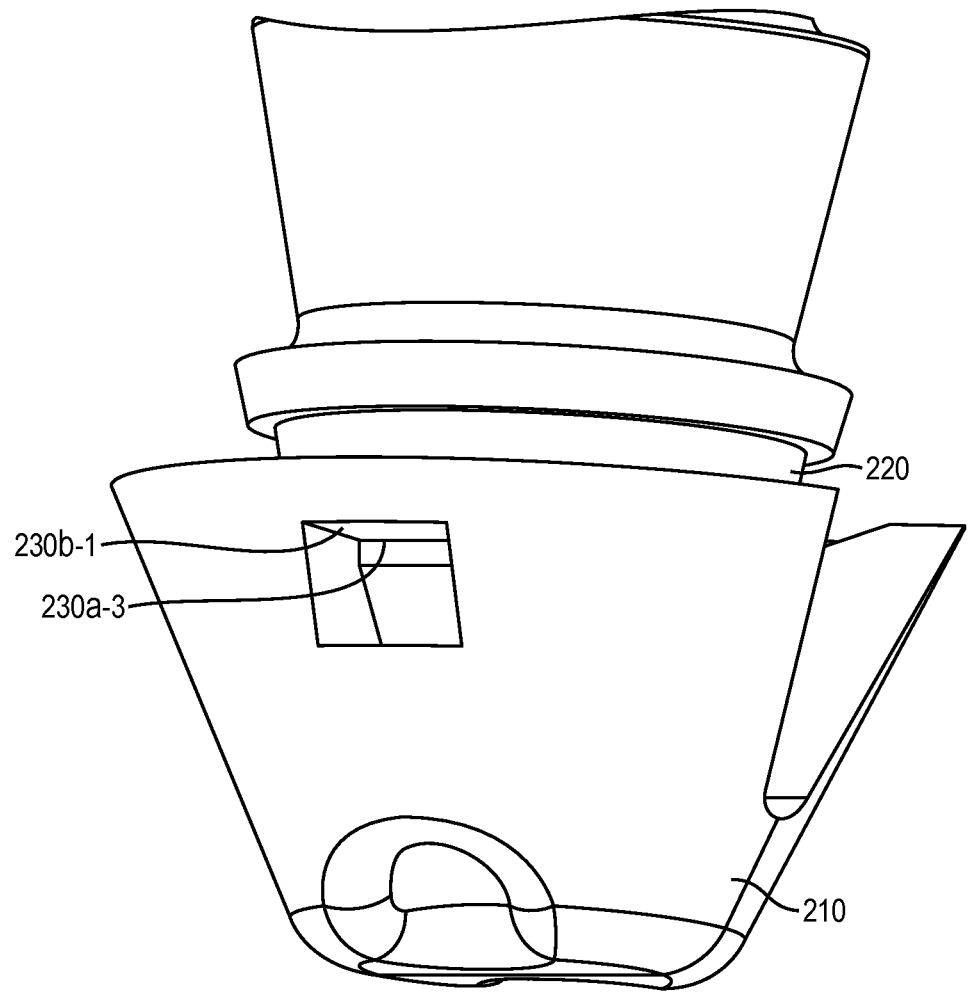

With reference to FIG. 5A, the non-expandable body 205 includes a distal end 220 similar to the distal end 120 described above with reference to FIG. 2. In a convenient example of the suture anchor 200, the retention features 230 include at least one locking insert tab 230a formed on a surface 235 of the distal end 220. The expandable cap 210 includes at least one holding insert tab 2301 configured to engage the locking insert tab 230a on the non-expandable body 205. The locking insert tab 230a includes an incline surface 230a-1 extending away from the surface 235 of the distal end 220 in the proximal direction. The inclined surface 230a-1 facilities the expandable cap 210 fitting over the distal end 220 of the non-expandable body 205. The locking insert tab 230a terminates at a shoulder 230a-2 having a proximal facing surface 230a-3. As more clearly shown in FIG. 5C, the proximal facing surface 230a-3 abuts a distal facing surface 230b-1 of the holding insert tab 230b and acts as a stop.

It should be readily apparent that other means and configurations for retaining the non non-expandable body 205 and expandable cap 210 are within the contemplation of this disclosure. For example, the placement of the locking insert tab 230a on the non-expandable body 205 and the holding insert tab 230b in the expandable cap 210 described above may be switched. Other examples of the retention features 230 include an annular protrusion formed around the distal end 220 and complementary annular groove formed in the cap 210, or vice versus.

Figure 5D:
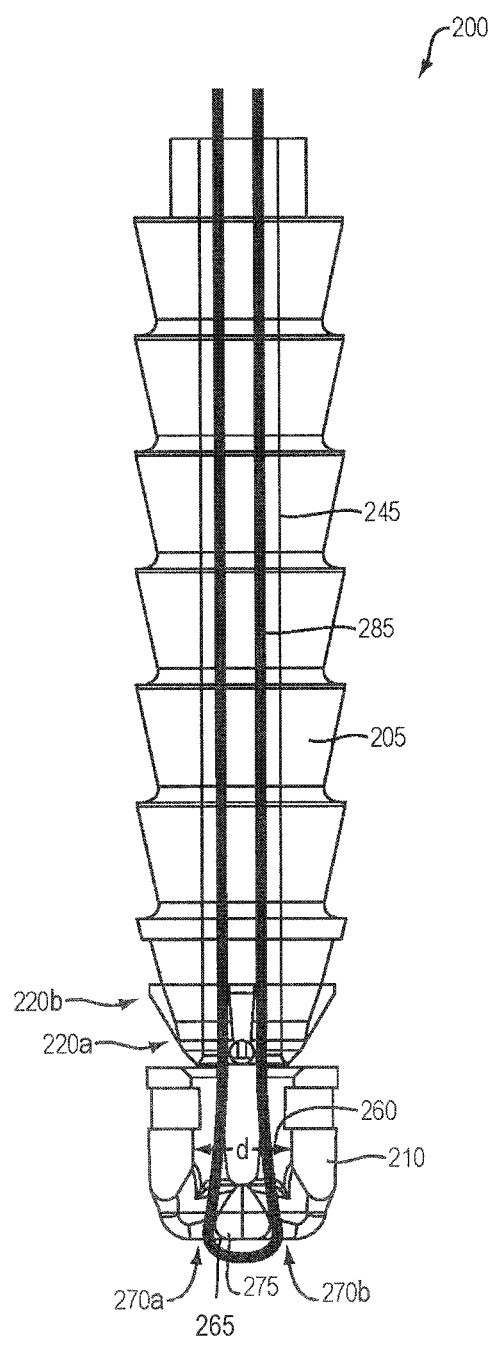

With reference to FIG. 5D, the distal end 220 includes a first portion 220a and second portion 220b that is proximal to the first portion 220a. The expandable cap 210 has a cavity 260. The cavity 260 has a diameter larger than the first portion 220a and smaller than the second portion 220b. In the example shown, a substantial portion (e.g., 60% to 90%) of the cavity 260 has a constant diameter of "d." Other examples of the cavity 260 may have geometry similar to the cavity 160 described above with reference to FIG. 2.

In some situations, as the non-expandable body 205 and expandable cap 210 are brought together, initially, the first portion 220a of the distal end does not contact the surface of the cavity 260. In an off-axis situation, in which the non-expandable body 205 and expandable cap 210 are not aligned with one another other (e.g., the longitudinal axis of each does not coincide with the other), the first portion 220a contacts a portion of the surface. In both situations, bringing the non-expandable body 205 and expandable cap 210 further together brings the second portion 220b and surface into contact with each other and centers the expandable cap 210 with respect to the non-expandable body 205. Advantageously, this arrangement corrects for any initial misalignment between the non-expandable body 205 and expandable cap 210.

The expandable cap 210 includes a terminal surface 265 adjacent tee the cavity 260. In a convenient example, the terminal surface 265 defines a first aperture 270a and second aperture 270b. A bridge 275 separates the first aperture 270a and second aperture 270h. A suture 285 extends around the bridge 275 and through a cannulation 245 in the expendable non-expandable body 205. This example is advantageous because it allows the suture to be passed distally through one aperture and proximally through the other aperture, negating the need for a knot.

Another example of the expandable cap 210 includes an axial hole that is co-axial with the cannulation 245 of the non-expandable body 205. A suture is threaded through the hole of the expandable cap 210. The suture has a distal knot that inhibits the suture from being pulled through the non-expandable body 205. Yet another example of the expandable cap 210 is formed, integrally, with a suture. A knot at the distal end 220 of the suture is overmolded with the expandable cap 210.

The suture anchor 200 includes an optional expansion slot that assists in the expansion of the expandable cap 210. A convenient example of the expansion slot is similar to the expansion slot 180 described above with reference to FIG. 3. In another example (not shown), the expansion slot cooperates with an optional side boss for aligning the expandable cap 210 and non-expandable body 205. For example, the optional side boss is inserted into the expansion slot. Advantageously, this inhibits the non-expandable body 205 from rotating about the expandable cap 210 and maintains the preferred orientation between the two.

Some examples of the suture anchors 100 and 200 are small-diameter anchors or "microanchors" having diameters on the order of 1 mm to 3 mm. Other examples include larger diameter anchors for use in different parts of the body. Examples of the suture anchors 100 and 200 may be completely or a portions thereof (e.g., the body) made from a formulation of poly(lactic-co-glycolic) acid (PLGA), ß-Tricalcium phosphate (ß-TCP) and calcium sulfate, poly-L-lactic acid-hydroxyapatite (PLLA-HA), polyether ether ketone (PEEK) or variants thereof. Biocomposite examples of suture anchors 100, 200, 400, 500, and 600 made from a combination of PLGA, ß-TCP, and calcium sulfate are absorbable by the body, which is beneficial to natural healing. An example formulation of PLGA, ß-TCP, and calcium sulfate is described in U.S. Pat. No. 8,545,866, the entirety of which is herein incorporated by reference. Other commonly used material for implants are also contemplated by this disclosure.

It is noted that the foregoing examples have been provided merely for the purpose of explanation and are in no way to be construed as limiting of the present invention. While the present invention has been described with reference to examples, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and examples, the present invention is not intended to be limited to the particulars disclosed herein; rather, the present invention extends to all functionally equivalent structures, methods and uses, such as are within the scope of the appended claims.

The invention claimed is:

1. A suture anchor comprising:
    a non-expandable body comprising:
        a distal end having a first portion and a second portion;
        a proximal end configured to engage a suture anchor insertion instrument;
        an internal cannulation extending from the distal end to the proximal end; and
        a plurality of projections extending, radially, from an outer surface between the distal end and proximal end, the plurality of projections configured to compress into bone;
    an expandable cap having a distal terminal surface comprising a first aperture and a second aperture, the expandable cap defining a cavity configured to engage the distal end of the non-expandable body, the cavity having a diameter larger than the first portion and smaller than the second portion that, when in a deployed position, allows the expandable cap to expand radially outward and compress into the bone during engagement of the distal end of the non-expandable body and the expandable cap; and
    a suture extending through the first and second apertures and from the cavity of the expandable cap, the suture being slidably received within the cannulation of the non-expandable body such that an eyelet portion of the suture extends from a proximal terminus of the cannulation external to the non-expandable body;
    wherein a distal end of the non-expandable body includes a ramp portion formed at an angle to a longitudinal axis of the non-expandable body, the geometry of the ramp portion and at least one of the plurality of projections being a truncated conical section comprising a distal first diameter and a proximal second diameter larger than the first diameter;
    wherein the expandable cap is configured such that a proximal force exerted on the expandable cap is effective to pull the distal end of the non-expandable body into the cavity of the expandable cap; and
    wherein, in the deployed position, the cavity of the expandable cap is configured to receive only the distal end of the non-expandable body such that the proximal end of the non-expandable body extends external to the cavity whereby at least one of the plurality of projections is external to the cavity and proximal to the expandable cap, and a distal terminus of the non-expandable body is disposed within the cavity.

2. The suture anchor of claim 1 wherein the first portion of the distal end does not engage a surface of the cavity; and the wherein the second portion of the distal end engages the surface of the cavity.

3. The suture anchor of claim 1 wherein the proximal end comprises one of a protrusion or recess configured to engage a complementary recess or protrusion, respectively, of a suture anchor insertion instrument.

4. The suture of claim 1 wherein the plurality of projections comprise a plurality of annular ribs each extending around an entire circumference of the non-expandable body.

5. The suture anchor of claim 1 wherein the cavity has a shape complementary to the distal end of the non-expandable body.

6. The suture anchor of claim 1 wherein the terminal surface is adjacent the cavity and defines the first aperture, the second aperture, and a bridge separating the first aperture and the second aperture; and wherein a portion of the suture extends around the bridge such that the portion of the suture is distal to the expandable cap, and a first free end and a second free of the suture are routed through the first aperture and second aperture, respectively, and through a through hole toward the proximal end of the non-expandable body.

7. The suture anchor of claim 6 wherein the first free end and the second free are coupled together.

8. The suture anchor of claim 1 wherein the expandable cap comprises a distal end and a proximal end; and further comprises at least one expansion slot formed in the proximal end of the expandable cap.

9. The suture anchor of claim 8 wherein the at least one expansion slot is aligned with the axis of the non-expandable body.

10. The suture anchor of claim 1 wherein the distal end of the non-expandable body further comprises a locking insert tab; and wherein the expandable cap further comprises a holding insert tab configured to engage the locking insert tab such that when the locking insert tab and holding insert tab are engaged, the expandable cap and the non-expandable body are locked together.

11. The suture anchor of claim 1 wherein the distal end of the non-expandable body comprises an annular protrusion; and wherein the expandable cap comprises an annular groove configured to engage the annular protrusion such that when the annular groove and annular protrusion are engaged, the expandable cap and the non-expandable body are locked together.

12. The suture anchor of claim 1 further comprising a post extending, axially, from the cavity of the expandable cap; and wherein the cannulation is configured to receive the post and align the non-expandable body and the expandable cap.

13. The suture anchor of claim 1 further comprising at least one protrusion formed on the outer surface of the non-expandable body at the distal end; and wherein the at least one expansion slot is configured to receive the at least one protrusion and align the non-expandable body and the expandable cap.

14. The suture anchor of claim 1 wherein the non-expandable body is made from a first material; and wherein the expandable cap is made from a second material more flexible than the first material.

15. The suture anchor of claim 1 wherein the non-expandable body has a diameter between 1 mm and 3 mm.

16. The suture anchor of claim 1 wherein the non-expandable body comprises a material selected from a formulation of poly(lactic-co-glycolic) acid (PLGA), ß-Tricalcium phosphate (ß-TCP) and calcium sulfate, poly-L- lactic acid-hydroxyapatite (PLLA-HA), polyether ether ketone (PEEK) or variants thereof.

17. The suture anchor of claim 1 wherein the cavity extends through the cap for less than an entire length of the cap.

18. The suture anchor of claim 1 wherein the suture is coupled to the expandable cap such that a proximal force exerted on the suture is effective to pull the expandable cap into the engagement with the distal end of the non-expandable body.

* * * * *